United States Patent
Hallier-Soulier et al.

(10) Patent No.: US 9,580,757 B2
(45) Date of Patent: Feb. 28, 2017

(54) **METHOD FOR DETERMINING THE PRESENCE OR ABSENCE OF SHIGA TOXIN-PRODUCING *ESCHERICHIA COLI* (STEC) IN A FOOD SAMPLE**

(71) Applicant: PALL GENEDISC TECHNOLOGIES, Bruz (FR)

(72) Inventors: Sylvie Hallier-Soulier, Bruz (FR); Yu Wang, North Grafton, MA (US); Christell Nahuet, Noyal-Châtillon-sur-Seiche (FR); Marilyne Rummelhard, Bourg-des-Comptes (FR); Sarah Jemmal, Bruz (FR); Sébastien Bouton, Plélan-le-Grand (FR); Valérie Van Wilder, Rennes (FR)

(73) Assignee: PALL GENEDISC TECHNOLOGIES, Bruz (FR)

( * ) Notice: Subject to any disclaimer, the term of this patent is extended or adjusted under 35 U.S.C. 154(b) by 272 days.

(21) Appl. No.: 14/466,417

(22) Filed: Aug. 22, 2014

(65) Prior Publication Data

US 2015/0072343 A1 Mar. 12, 2015

(30) Foreign Application Priority Data

Sep. 3, 2013 (EP) .................................... 13182864

(51) Int. Cl.
*C12Q 1/68* (2006.01)

(52) U.S. Cl.
CPC .......... *C12Q 1/689* (2013.01); *C12Q 2600/158* (2013.01)

(58) Field of Classification Search
None
See application file for complete search history.

(56) References Cited

U.S. PATENT DOCUMENTS

2002/0081669 A1    6/2002   Festoc

FOREIGN PATENT DOCUMENTS

| WO | WO 02/09877 A1   | 2/2002 |
| WO | WO 2011/018762 A1 | 2/2011 |
| WO | WO 2013/029021   | 2/2013 |

OTHER PUBLICATIONS

Wasilenko et al. Journal of Food Protection 2012; 75: 1939-1950.*
L. Vold et al., "Occurrence of shigatoxinogenic *Escherichia coli* O157 in Norwegian cattle herds," *Epidemiology and Infection*, 120(1): 21-28 (1998).
European Search Report, Application No. 13 182 864.2, dated Nov. 28, 2013.
Fratamico, P. et al., "Detection by multiplex real-time polymerase chain reaction assays and isolation of shiga toxin-producing *Escherichia coli* serogroups O26, O45, O103, O111, O121, and O145 in ground beef," Foodborne Pathogens and Disease, 8(5), 601-607 (2011).
Fratamico, P. et al., "Detection of shiga toxin-producing *Escherichia coli* inground beef using the genedisc real-time PCR system," *Frontiers in Cellular and Infection Microbiology*. 2, 1-6 (2012).
"GeneDisc Cycler: an easy, rapid, reliable method for pathogen detection," Pall Life Sciences (2011).
Madic, J. et al., "Detection of shiga toxin-producing *Escherichia coli* serotypes O26:H11, O103:H2, O111:H8, O145:H28, and O157:H7 in raw-milk cheeses by using multiplex real-time PCR," *Applied and Environmental Microbiology*, 77(6), 2035-2041 (2011).
Nielsen E. M. et al., "Detection and characterization of verocytotoxin-producing *Escherichia coli* by automated 5' nuclease PCR assay," *J. Clinical Microbiology*, 41(7), 2884-2893 (2003).
ISO/TS 13136:2012 "Microbiology of food and animal feed- Real-time polymerase chain reaction (PCR)-based method for the detection of food-borne pathogens-Horizontal method for the detection of shiga toxin-producing *Escherichia coli* 9STEC) and the determination of O157, O111, O26, O103 and O145 serogroups," International Organization for Standardization (Abstract).

* cited by examiner

*Primary Examiner* — Angela M Bertagna
(74) *Attorney, Agent, or Firm* — Leydig, Voit & Mayer (57) ABSTRACT

A method for detecting the presence or absence of pathogenic. STEC in food samples includes
  incubating the food sample in a culture medium to obtain an *E. coli* stock medium;
  lysing the *E. coli* to obtain a *E. coli* DNA; and
  subjecting the DNA to PCR, and amplifying the following genes or fragments thereof:
    stx1 and/or stx2 encoding Shiga toxin 1 and Shiga toxin 2,
    for each STEC serogroup to be determined, the subtype of the eae gene of that serogroup encoding an intimin, and
    for each STEC serogroup to be determined, a biomarker gene specific for that serogroup;
  and, if stx1 and/or stx2 and the eae gene and the specific biomarker gene for at least one serogroup are amplified in the PCRs:
    verifying the presence of the one or more specific serogroups of STEC by PCRs on concentrates of the *E. coil* stock medium.

18 Claims, 5 Drawing Sheets

SEQUENCE LISTING

<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
cttgcaaatc gttctttggg                                        20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tagcggtacg actgtcttgg                                        20

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3 tcaaaccota acctcagctc cagc                                    24

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
tgtacgcgac ggcagaga                                           18

<210> SEQ ID NO 5
<211> LENGTH: 26
<212> TYPE: DNA
<213> ORGANISM: Artificial Sequence
<220> FEATURE:
<223> OTHER INFORMATION: Synthetic

<400> SEQUENCE: 5
ggcaggcttt tatattctcc aacttt                                  26

<210> SEQ ID NO 6
<211> LENGTH: 31
<212> TYPE: DNA
<213> ORGANISM: Artificial Sequence
<220> FEATURE:
<223> OTHER INFORMATION: Synthetic

<400> SEQUENCE: 6
accccgttaa atcaatacta tttcacgagg t                            31

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
ctttcgttgc gttgtgcatg                                         20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
gtaatgcgac agatatggcc                                         20

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
ttttgctgca agtgggctgt cc                                      22

<210> SEQ ID NO 10

```
<211> LENGTH: 23
<212> TYPE: DNA
<213> ORGANISM: Artificial Sequence
<220> FEATURE:
<223> OTHER INFORMATION: Synthetic

<400> SEQUENCE: 10
aaggtgatta cgaaaatgca tgt                                            23

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
ccaaaaaagc accccgtac ttat                                            24

<210> SEQ ID NO 12
<211> LENGTH: 29
<212> TYPE: DNA
<213> ORGANISM: Artificial Sequence
<220> FEATURE:
<223> OTHER INFORMATION: Synthetic

<400> SEQUENCE: 12
ttggcgtgca tcaattaaat tatccttca                                      29

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13
gaggcaacac attatatagt gcttt                                          25

<210> SEQ ID NO 14
<211> LENGTH: 26
<212> TYPE: DNA
<213> ORGANISM: Artificial Sequence
<220> FEATURE:
<223> OTHER INFORMATION: Synthetic

<400> SEQUENCE: 14
gcttggtgtt tagttagcca aaggta                                         26

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
aatctcccag atgatcaaca tcgtgaa                                        27

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
```

```
gcttcttatc tggactggtg                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ccaatggcat acaatgagag                                              20

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
agaagtttca gcaagtgcat cgcc                                         24

<210> SEQ ID NO 19
<211> LENGTH: 26
<212> TYPE: DNA
<213> ORGANISM: Artificial Sequence
<220> FEATURE:
<223> OTHER INFORMATION: Synthetic

<400> SEQUENCE: 19
cgataatatt taccccacca gtacag                                       26

<210> SEQ ID NO 20
<211> LENGTH: 15
<212> TYPE: DNA
<213> ORGANISM: Artificial Sequence
<220> FEATURE:
<223> OTHER INFORMATION: Synthetic

<400> SEQUENCE: 20
gccgccgcaa tgctt                                                   15

<210> SEQ ID NO 21
<211> LENGTH: 27
<212> TYPE: DNA
<213> ORGANISM: Artificial Sequence
<220> FEATURE:
<223> OTHER INFORMATION: Synthetic

<400> SEQUENCE: 21
ccgccattca gaatgcacac aatatcg                                      27

<210> SEQ ID NO 22
<211> LENGTH: 22
<212> TYPE: DNA
<213> ORGANISM: Artificial Sequence
<220> FEATURE:
<223> OTHER INFORMATION: Synthetic

<400> SEQUENCE: 22
caacagtctt gtacaagtcc ac                                           22

<210> SEQ ID NO 23
<211> LENGTH: 24
<212> TYPE: DNA
```

```
<213> ORGANISM: Artificial Sequence
<220> FEATURE:
<223> OTHER INFORMATION: Synthetic

<400> SEQUENCE: 23
cgatgagttt atctgcaagg tgat                                              24

<210> SEQ ID NO 24
<211> LENGTH: 30
<212> TYPE: DNA
<213> ORGANISM: Artificial Sequence
<220> FEATURE:
<223> OTHER INFORMATION: Synthetic

<400> SEQUENCE: 24
aggaccgcag aggaaagaga ggaattaagg                                        30

<210> SEQ ID NO 25
<211> LENGTH: 25
<212> TYPE: DNA
<213> ORGANISM: Artificial Sequence
<220> FEATURE:
<223> OTHER INFORMATION: Synthetic

<400> SEQUENCE: 25
ggtgataatc agagtgcgac ataca                                             25

<210> SEQ ID NO 26
<211> LENGTH: 26
<212> TYPE: DNA
<213> ORGANISM: Artificial Sequence
<220> FEATURE:
<223> OTHER INFORMATION: Synthetic

<400> SEQUENCE: 26
ggcatcaaaa tacgtaactc gagtat                                            26

<210> SEQ ID NO 27
<211> LENGTH: 29
<212> TYPE: DNA
<213> ORGANISM: Artificial Sequence
<220> FEATURE:
<223> OTHER INFORMATION: Synthetic

<400> SEQUENCE: 27
ccacagcaat tacaatacta cccggtgca                                         29

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
ctgttagtgc gacagtcagt ga                                                22

<210> SEQ ID NO 29
<211> LENGTH: 27
<212> TYPE: DNA
<213> ORGANISM: Artificial Sequence
<220> FEATURE:
<223> OTHER INFORMATION: Synthetic

<400> SEQUENCE: 29
gctgttgtca attttcagtt catcaaa                                           27
```

```
<210> SEQ ID NO 30
<211> LENGTH: 26
<212> TYPE: DNA
<213> ORGANISM: Artificial Sequence
<220> FEATURE:
<223> OTHER INFORMATION: Synthetic

<400> SEQUENCE: 30
tggggctgag gttaaagcga ctgagg                                          26

<210> SEQ ID NO 31
<211> LENGTH: 28
<212> TYPE: DNA
<213> ORGANISM: Artificial Sequence
<220> FEATURE:
<223> OTHER INFORMATION: Synthetic

<400> SEQUENCE: 31
ggtgttaaag cacctgaggt tacatttt                                        28

<210> SEQ ID NO 32
<211> LENGTH: 24
<212> TYPE: DNA
<213> ORGANISM: Artificial Sequence
<220> FEATURE:
<223> OTHER INFORMATION: Synthetic

<400> SEQUENCE: 32
caccagtaac gttcttacca agaa                                            24

<210> SEQ ID NO 33
<211> LENGTH: 30
<212> TYPE: DNA
<213> ORGANISM: Artificial Sequence
<220> FEATURE:
<223> OTHER INFORMATION: Synthetic

<400> SEQUENCE: 33
tcaaccttgt tgtcaatttt cagtccatca                                      30

<210> SEQ ID NO 34
<211> LENGTH: 27
<212> TYPE: DNA
<213> ORGANISM: Artificial Sequence
<220> FEATURE:
<223> OTHER INFORMATION: Synthetic

<400> SEQUENCE: 34
gggaaattct aatacccaaa ttgtgaa                                         27

<210> SEQ ID NO 35
<211> LENGTH: 23
<212> TYPE: DNA
<213> ORGANISM: Artificial Sequence
<220> FEATURE:
<223> OTHER INFORMATION: Synthetic

<400> SEQUENCE: 35
actaacaaca gcattacctg caa                                             23

<210> SEQ ID NO 36
<211> LENGTH: 24
<212> TYPE: DNA
<213> ORGANISM: Artificial Sequence
<220> FEATURE:
```

<223> OTHER INFORMATION: Synthetic

<400> SEQUENCE: 36
cactaacaat agcattacct gcaa					24

<210> SEQ ID NO 37
<211> LENGTH: 29
<212> TYPE: DNA
<213> ORGANISM: Artificial Sequence
<220> FEATURE:
<223> OTHER INFORMATION: Synthetic

<400> SEQUENCE: 37
ccagatgtca gttttaccgt agccctacc					29

<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38
gcctgtgaca gctgaagctt tacg					24

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
gctgtcacag cagaagcctt acg					23

<210> SEQ ID NO 40
<211> LENGTH: 22
<212> TYPE: DNA
<213> ORGANISM: Artificial Sequence
<220> FEATURE:
<223> OTHER INFORMATION: Synthetic

<400> SEQUENCE: 40
ccccagttca atgtaagatc aa					22

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
ccagttcaga gtgaggtcca					20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
ccagttcagt gtgaggtcca					20

```
<210> SEQ ID NO 43
<211> LENGTH: 27
<212> TYPE: DNA
<213> ORGANISM: Artificial Sequence
<220> FEATURE:
<223> OTHER INFORMATION: Synthetic

<400> SEQUENCE: 43
aggagcagtt tcagacagtg cctgacg                                        27

<210> SEQ ID NO 44
<211> LENGTH: 28
<212> TYPE: DNA
<213> ORGANISM: Artificial Sequence
<220> FEATURE:
<223> OTHER INFORMATION: Synthetic

<400> SEQUENCE: 44
tcatccagtg ttgtacgaaa tcccctct                                       28
```

METHOD FOR DETERMINING THE PRESENCE OR ABSENCE OF SHIGA TOXIN-PRODUCING *ESCHERICHIA COLI* (STEC) IN A FOOD SAMPLE

FIELD OF THE INVENTION

The present invention relates to a method for determining the presence or absence of Shiga toxin-producing *Escherichia coli* (STEC) in food samples, a reaction cartridge to be used in such method, and an apparatus to accommodate the reaction cartridge.

BACKGROUND OF THE INVENTION

Among the strains of STEC, seven serogroups, i.e., O157, O26, O45, O103, O111, O121, and O145, have been identified to be associated with severe illness in humans. These serogroups are referred to in the following as STEC Top7. The United States Department of Agriculture (USDA) has implemented regulations applicable to the analysis of certain raw beef products which define in addition to the serogroup O157 six further serogroups as identified above as adulterants.

When determining the presence or absence of these strains of STEC, typically a food sample is added to a culture medium enabling growth of *E. coli* to provide an *E. coli* stock medium.

Subsequently, lysis of the *E. coli* in the stock medium provides for a sample solution comprising *E. coli* DNA.

The subsequent detection of the above-mentioned serogroups in the samples in a reliable manner using conventional methods is a time consuming procedure.

The use of polymerase chain reaction (PCR) for detecting the major STEC virulence genes stx1, stx2, eae, and serogroup-specific genes is set out in the ISO 13136 technical specification (ISO/TS 13136:2012). PCR positive samples have to be confirmed by cultural methods as the different genes could belong to different strains, leading to false positive results.

BRIEF SUMMARY OF THE INVENTION

The object of the present invention is to provide a method which will lead within a shorter period of time to reliable results with respect to the presence or absence of pathogenic STEC in food samples.

This object is solved by a method as set out in claim 1.

Surprisingly, because of its specific workflow the method according to the present invention allows both a decrease of the rate of false positive results as well as an optimization of colony isolation. Thereby the determination of the presence or absence of one or more specific serogroups of Shiga toxin-producing *E. coli* (STEC) in a food sample can be remarkably simplified.

More specifically, the present invention provides a method for the identification and confirmation of the presence or absence of highly pathogenic STEC in food samples in a very time efficient manner in that, after an *E. coli* stock medium is obtained by incubating the food sample in a culture medium and the lysis of the *E. coli* contained in the stock medium, this DNA containing sample solution is subjected to a first series of PCR using specific primers. This may be called a first screening step. This first screening step allows the simultaneous detection of stx1 and/or stx2 virulence genes encoding for Shiga toxins, the eae subtype encoding for an intimin specifically associated with one or more serogroups, and the biomarker gene of each serogroup.

Subsequently, presumptive positive samples will have to be confirmed.

The detection of the eae subtypes allows to substantially reduce the number of false positive samples.

In a preferred embodiment, the positive samples are subjected to a second screening step, wherein an immuno-concentrate derived from the *E. coli* stock medium is checked once again in a PCR analysis.

In case this second screening step yields positive results, part of the immunoconcentrate is plated on chromogenic media in order to isolate the respective STEC strain as colonies.

The DNA derived from these isolated colonies may be PCR tested to confirm the presence of both stx and eae virulence genes, and optionally the serogroup biomarker genes.

In case of negative samples, the final results are available within about 12 h starting off from the food sample. In case of positive samples the final results are available in about 2 days.

The invention furthermore relates to reaction cartridges according to claim 13 designed to be used in the inventive method outlined above.

Another aspect of the present invention resides in an apparatus defined in claim 15.

DETAILED DESCRIPTION OF THE INVENTION

Preferably, the method of the present invention includes verification of the presence of the one or more specific serogroups of STEC comprising
  performing an immunoconcentration of the culture medium with the incubated food sample for each serogroup, using antibodies directed against the STEC of the respective serogroup;
  isolating DNA from the immunoconcentrates; and
  subjecting the DNA to a second series of PCRs, using primers to amplify the following *E. coli* genes or fragments thereof:
    stx1 and/or stx2,
    the subtypes of the eae genes of the respective serogroups, and
    optionally, the biomarker genes specific for the respective serogroups.

More preferably, the verification of the presence of the one or more specific serogroups of STEC further comprises, in case that stx1 and/or stx2 as well as the eae genes are amplified in the second series of PCRs:
  plating the immunoconcentrates on a chromogenic medium to enable growth of isolated *E. coli* colonies;
  isolating DNA from the Isolated colonies; and
  subjecting the DNA to a third series of PCRs, using primers to amplify the following *E. coli* genes or fragments thereof:
    stx1 and/or stx2,
    the subtypes of the eae genes of the respective serogroups, and
    optionally, the biomarker genes specific for the respective serogroups.

Preferably, the series of PCRs are performed with specific labeled DNA probes to allow a detection of the amplified genes or fragments thereof.

According to the present invention the specific serogroup(s) to be determined are preferably selected from O157, O26, O45, O103, O111, O121 and O145.

While the method of the present invention allows identifying of one or several of the specific serogroups, more preferably the method comprises the determination of the presence or absence of all serogroups O157, O26, O45, O103, O111, O121 and O145 in one step.

It is furthermore preferred to select the subtypes of the eae gene to be amplified in the series of PCRs from eae β for O26, eae γ for O145 and O157, eae ε for O45, O103 and O121, and eae θ for O111.

When performing the method of the present invention, preferably the specific biomarker genes are selected from the O-antigen transporter genes of the respective serogroups.

While the method of the present invention is applicable to a broad range of food samples, preferably the food sample is selected from raw meat, a raw dairy product, or a raw vegetable product, in particular a sprout.

The culture medium used for the incubation step preferably is selected from buffered peptone water, optionally comprising acriflavine; tryptic soy broth (TSB), optionally comprising novobiocine; and modified tryptic soy broth (mTSB), optionally comprising novobiocine.

The method of the present invention performs the PCRs of each series preferably simultaneously in an automated manner, such that the device used for the PCRs allows an automatic evaluation and indication of the final result.

In accordance with a preferred variant of the method of the present Invention the antibodies used for the immuno-concentration are selected from monoclonal antibodies or polyclonal antibodies.

The chromogenic medium used for plating the immuno-concentrates is preferably selected from Cefixime-Tellurite Sorbitol McConkey (CT-SMAC); modified Rainbow Agar (mRBA) comprising novobiocine, cefixime trihydrate and potassium tellurite; Tryptone Bile X Glucuronide medium (TBX); and Cefixime-Tellurite Rhamnose McConkey (CT-RMAC).

The present invention also relates to a reaction cartridge specifically adapted to be used in the method of the present invention.

Such reaction cartridge is designed for performing a series of PCRs on a DNA-containing sample solution and comprises a plurality of reaction chambers and a reservoir. The sample solution can be fed into the reservoir and homogeneously distributed into the reaction chambers via conduits connecting each reaction chamber with the reservoir. At least some of the reaction chambers are preloaded with primers and probes to amplify the following E. coli genes or fragments thereof:
  stx1 and/or stx2,
  the subtypes of the eae gene of one or more serogroups selected from O157, O26, O45, O103, O111, O121 and O145, and
  optionally, biomarker genes specific for one or more serogroups selected from O157, O26, O45, O103, O111, O121 and O145.

Furthermore, the invention also relates to an apparatus for automatically performing a series of PCRs, wherein this apparatus is adapted to accommodate the above-mentioned reaction cartridge. The apparatus comprises
  detection means for detecting the amplified E. coli genes with the aid of the respective probes;
  control means for controlling the performance of the PCRs, wherein a software is stored in the control means which is able to evaluate the detected E. coli genes according to an algorithm, such that a final result is generated for each serogroup depending on the detection results for stx1 and/or stx2, for the subtypes of the eae gene of that serogroup, and optionally for the biomarker gene specific for that serogroup; and
  display means for optically and/or acoustically indicating the final result for each serogroup.

The afore-mentioned aspects and advantages of the present invention will be disclosed in more detail below in connection with the drawings and specific examples.

DETAILED DESCRIPTION OF THE DRAWINGS AND EXAMPLES

Figure 1:
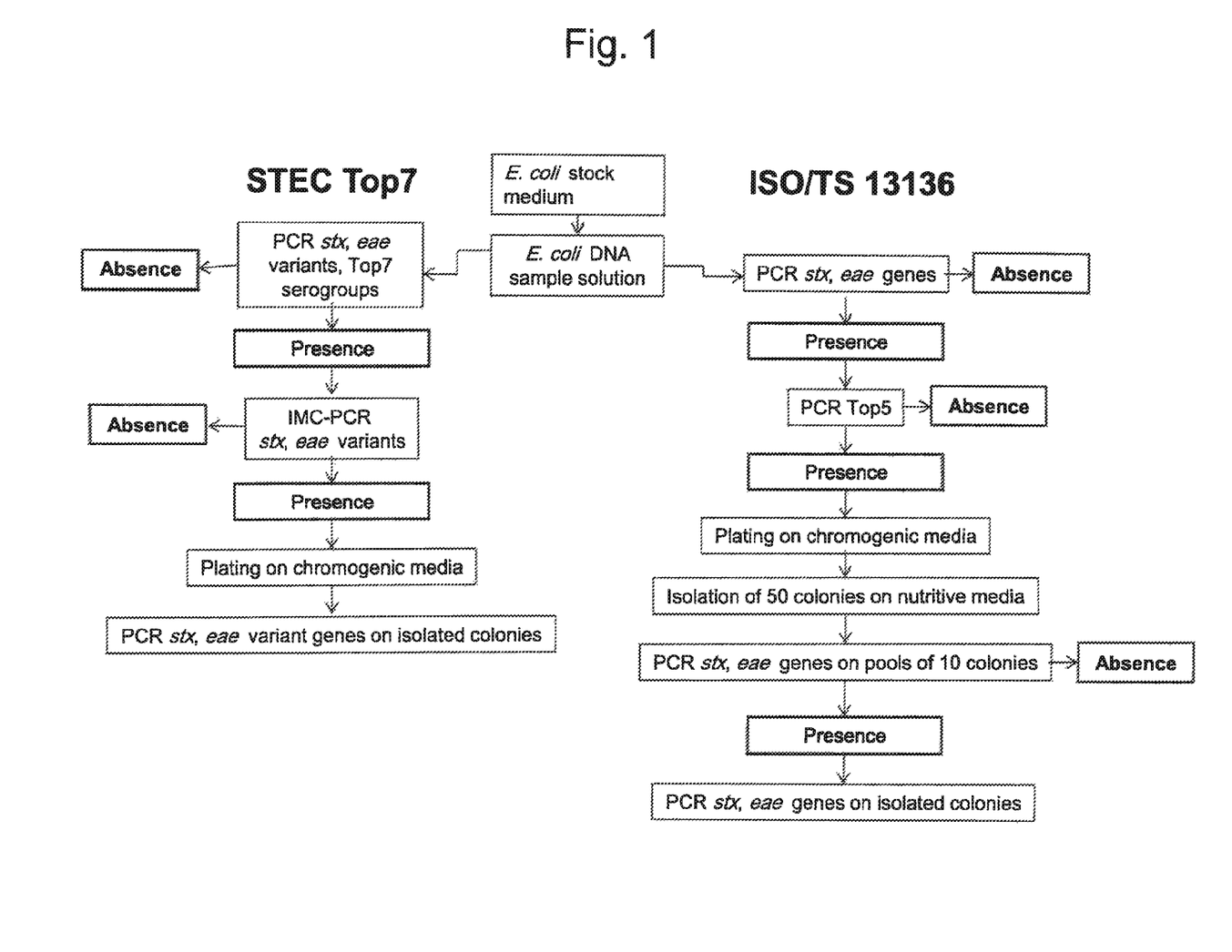
FIG. 1 shows the inventive method in comparison with a prior art method (ISO 13136 technical specification)

FIG. 1 shows on the left hand side a preferred workflow for the method of the present invention titled STEC Top7. On the right hand side a conventional worflow corresponding to ISO/TS 13136:2012 is shown.

Both methods start off with a food sample which has been incubated in a culture medium enabling growth of E. coli resulting in an enriched sample (E. coli stock medium).

Subsequently lysis of the E. coli grown in the culture medium is performed, e.g., in a lysis plate of 96 tubes (not shown) in order to obtain a sample solution comprising E. coli DNA.

So far the procedure is the same for the inventive method and the conventional workflow.

According to the inventive workflow, the sample solution is subjected to a first series of polymerase chain reactions (PCR), using primers and probes to amplify the specific E. coli genes or fragments thereof. Preferably, as indicated in FIG. 1, the workflow encompasses at this step the amplification of all STEC Top7, i.e., stx1, stx2, eae variants (subtypes) and biomarker genes for each of O157, O26, O45, O103, O111, O121 and O145. In the absence of any of these serogroups, the inventive workflow is terminated within a period of about 12 h or less (about 11 h for the incubation and lysis and about 1 h for the PCR).

In case positive results are reported, immunoconcentrates of the E. coli stock medium are prepared using antibodies directed against the STEC of the respective one or more serogroups, followed by
  isolating DNA from the immunoconcentrates; and
  subjecting the DNA to a second series of PCRs, using primers to amplify the following E. coli genes or fragments thereof:
    stx1 and/or stx2,
    the subtype of the eae genes of the respective serogroups, and
    optionally, the biomarker genes specific for the respective serogroups.

If negative results are obtained the workflow may be terminated.

In case positive results are obtained, preferably the immunoconcentrates are in addition plated on a chromogenic medium to enable growth of isolated E. coli colonies. In a further step, DNA is isolated from the isolated colonies and subjected in a third series of PCRs using primers to amplify E. coli genes or fragments thereof. Thereby the serogroup of pathogenic STEC may be identified. In such case the final results are available in about 2 days or less.

The workflow according to the conventional ISO/TS 13136:2012 differs from the inventive method in that the first screening is directed to stx and the generic eae genes. In the second screening step only the STEC Top5 are covered whereas the method of the present invention may cover all of the Top7 serogroups.

The conventional workflow needs about 24 h in case only negative results are obtained at the first stage. In case positive results have to be confirmed the workflow takes about 4 days.

Figure 2:
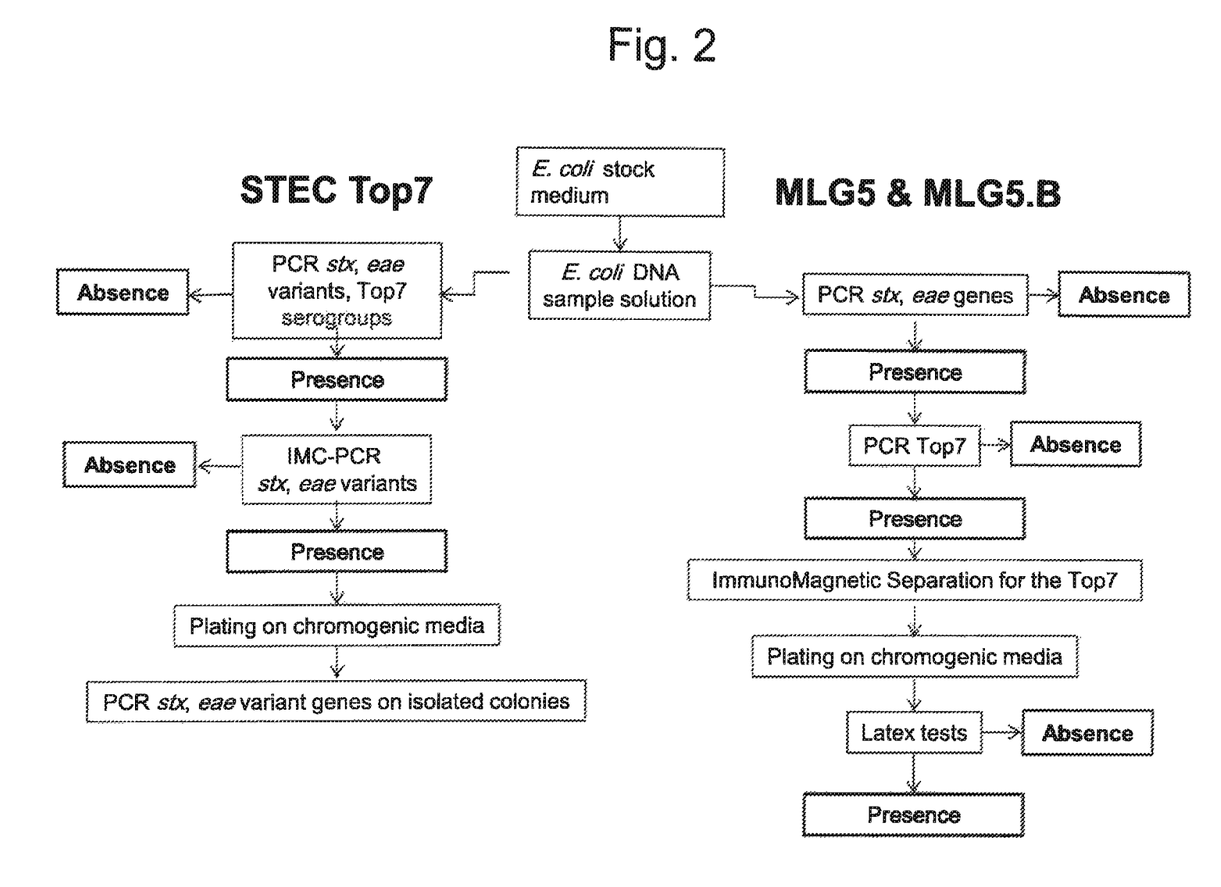
FIG. 2 shows the inventive method in comparison with a further prior art method.

FIG. 2 shows the method of the present invention in comparison with the method as proposed by the Microbiology Laboratory Guidebook of the US-Department of Agriculture, $3^{rd}$ Edition, 1998 (MLG 5 & MLG 5B.01), which needs about 24 h in case only negative results are obtained and about 3 days to confirm positive results.

Figure 3:
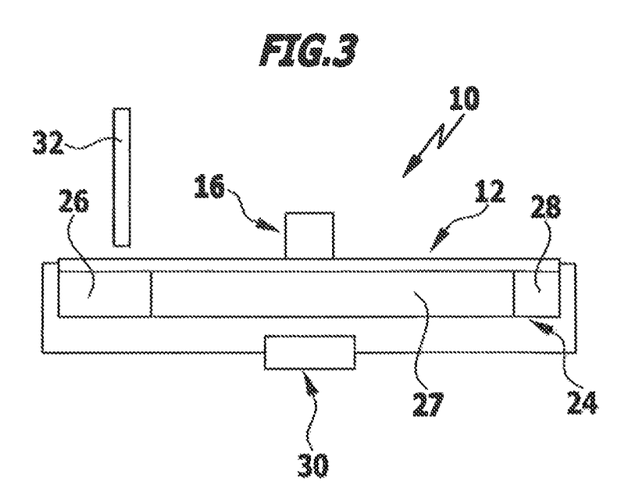
FIG. 3 shows a schematic representation of an apparatus for a PCR analysis according to the present invention.

FIG. 3 shows a schematic representation of an apparatus 10 suitable for carrying out the PCRs of the inventive method.

The apparatus 10 comprises a reaction cartridge 12 of a preferably disc-shaped configuration having a plurality of reaction chambers or wells 14 at the outer periphery thereof and a reservoir 16 in a central position, said reaction chambers 14 being connected to the reservoir via radially extending channels 18.

Figure 4:
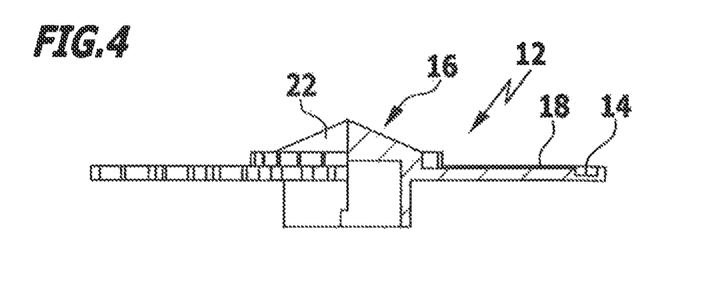
FIG. 4 shows a cross-sectional view of a PCR reaction cartridge of the present invention.
Figure 5:
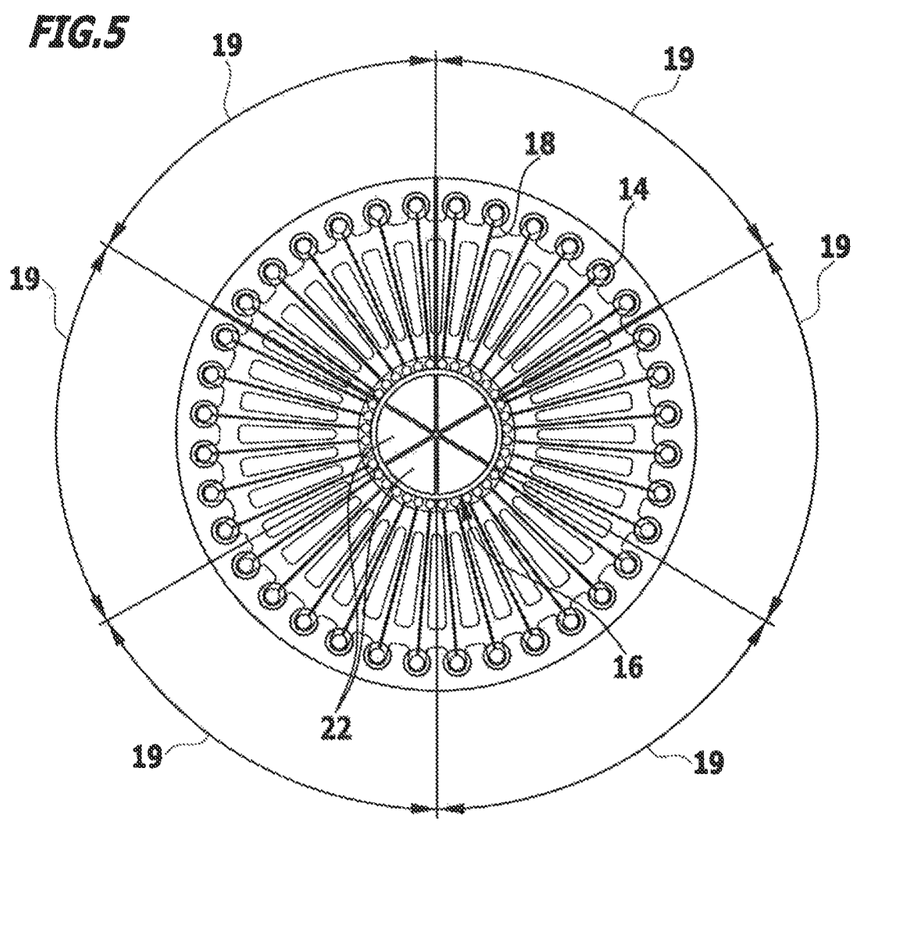
FIG. 5 shows a top view of the PCR reaction cartridge of the present invention.

Such a preferred reaction cartridge 12, which is also referred to as "GeneDisc" in the following, is shown in more detail in FIGS. 4 and 5.

A typical number of wells 14 of a reaction cartridge 12 is thirty-six. The wells 14 may be grouped in a plurality of sectors 19, e.g., six sectors (referred to as GeneDisc sectors). The wells 14 of a group of a sector 19 may be connected via individual channels 18 to a common partition 22 of the reservoir 16.

Such a cartridge 12 may be modified to provide a cartridge of the present invention wherein at least some of the reaction chambers 14 are preloaded with primers and probes to amplify stx1 and/or stx2, and the subtypes of the eae gene of one or more serogroups selected from O157, O26, O45, O103, O111, O121 and O145, or fragments of the respective genes. Preferably, reaction chambers 14 are also preloaded with primers and probes to amplify the biomarker genes specific for one or more of these serogroups.

The apparatus 10 further includes a preferably ring-shaped heating device 24 having four distinct zones (of which three zones 26, 27, 28 are visible) that can be heated to four different temperatures. The reaction cartridge 12 is placed on top of the heating device 24. The wells 14 of the reaction cartridge 12 are positioned close to or in contact with the heating device 24.

The apparatus 10 includes means 30 for rotating the reaction cartridge 12 with respect to the heating device 24 allowing a cyclic variation in the temperature of the reaction chambers or wells 14.

The temperature in each zone of the heating device 24 can be homogeneous or, if necessary, the temperature can vary along a gradient.

The apparatus 10 further includes fluorescence excitation and detection means 32 disposed above the cartridge 12 so as to excite and measure the fluorescence of the contents of the reaction chambers 14 for each cycle.

Such an apparatus 10 is disclosed in detail in WO 2002/009877 A1 and is available as GeneDisc Cycler (Pall GeneDisc Technologies).

Usually, each PCR cycle requires a first phase where the wells are heated to a temperature of about 95° C. to denature the target DNA, then a second phase with a temperature of about 55° C. to about 65° C. for primer annealing, and a third phase for elongation of the DNA-strands, normally carried out at about 72° C. However, PCR can be carried out with simplified cycles in accordance with the inventive method, in which annealing and elongation are carried out at the same temperature, such that each cycle requires only two different temperatures. The individual zones of the heating device 24 of the apparatus 10 are set to achieve such temperatures.

Preferably, primers and probes specific for the target sequences to be amplified are pre-distributed in the reaction chambers or wells 14. The reservoir 16 or its partitions is/are intended to receive a fluid composed of a sample of nucleic acids to be analyzed and the reagents required for a polymerase chain amplification reaction, with the exception of primers and probes.

In a preferred variation, it is possible to distribute, from a reservoir, a fluid containing a sample of nucleic acids to be analyzed and the reagents necessary for PCR in a plurality of reaction chambers containing specific primers and probes for the target nucleic acid sequences to be amplified, and to cause the amplification process by continuously subjecting the contents of the chambers to different temperatures in succession (namely those required for denaturation, annealing and elongation) a plurality of times by means of a cyclic relative movement of the reaction cartridge 12 including said reaction chambers 14 and said heating device 24 having four distinct zones that can be heated to different temperatures.

If necessary, the reaction chambers 14 can contain the reagents necessary for a real-time PCR reaction other than the primers mentioned above. In a preferred embodiment of the apparatus, the reaction chambers 14 also comprise, in addition to the primers, one or more probes that are specific to the sequence to be amplified. The distribution of the probes in the reaction chambers 14 can also be such that certain chamber comprise probes specific to the sequences to be amplified and other chamber comprise control probes, which do not a priori recognize the sequence to be amplified. These probes can be labelled and, if a plurality of probes are present in one and the same reaction chamber (for example a probe specific to the sequence to be amplified and a control probe), these probes will preferably be labelled with different fluorophores.

Preferably, the PCR reactions are carried out and evaluated by the apparatus 10 in an automated manner, i.e., without need for a user intervention after the reaction cartridge 12 has been inserted into the apparatus 10. With the aid of the fluorescence-labelled probes, the amplified sequences can be detected by the detection means 32 as mentioned above, and the result for each sequence to be amplified can be indicated to the user.

In a preferred embodiment, the apparatus 10 is modified according to the present invention and further comprises control means which not only control the performance of the PCRs, but also serve to evaluate the amplified sequences detected by the detection means 32 to provide the user with a final result.

When performing the inventive method, the input signals from the detection means 32 corresponding to the detected *E. coli* genes are evaluated according to an algorithm, such that a final result is generated by the modified apparatus 10 for each serogroup depending on the detection results for stx1 and/or stx2, for the subtypes of the eae gene of that serogroup, and optionally for the biomarker gene specific for that serogroup.

Figure 6:
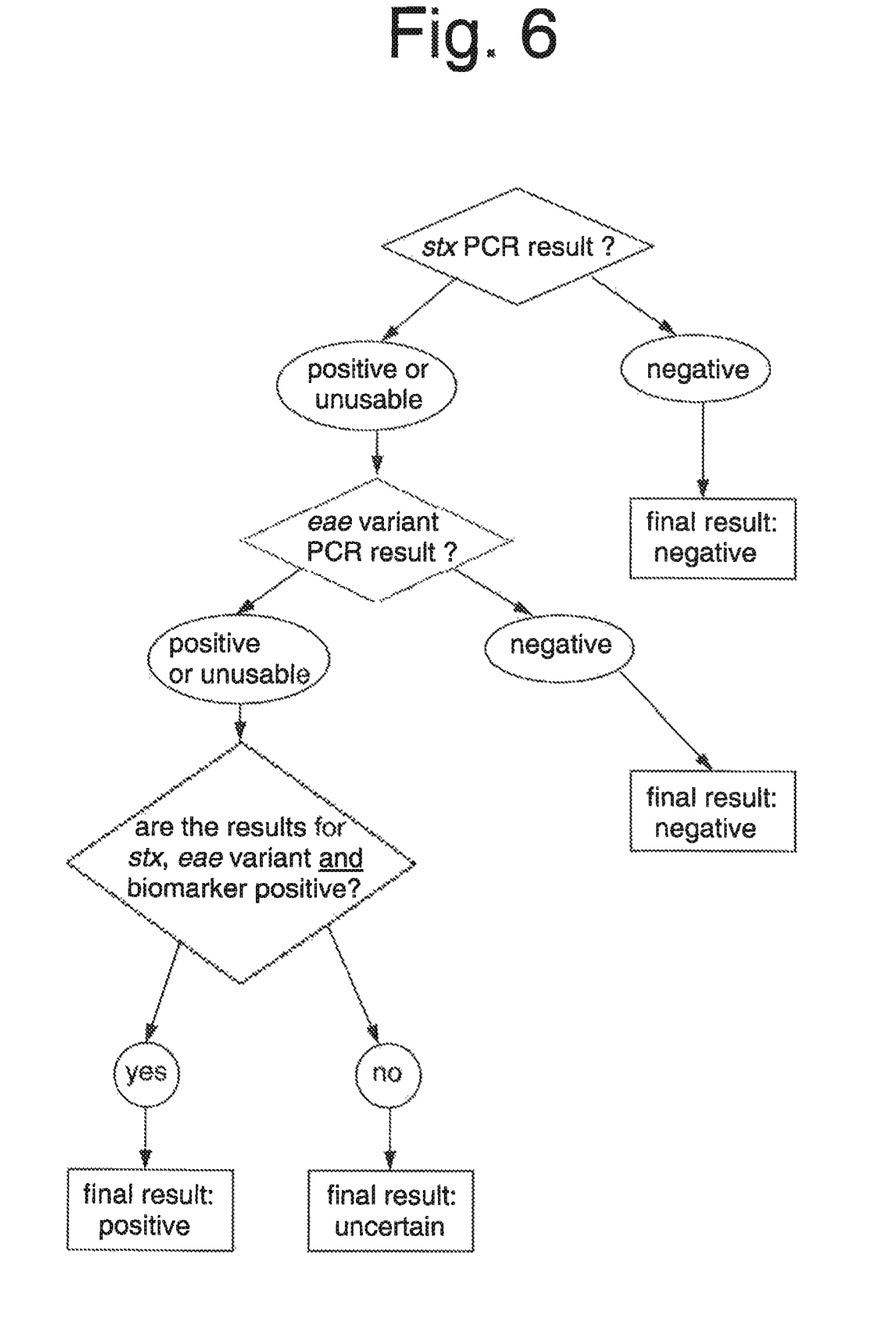
FIG. 6 shows a flow diagram of an algorithm for generating a final result as a function of PCR results.

A simplified flow diagram of a preferred algorithm implemented in the modified apparatus 10 is shown in FIG. 6. In this case, PCR results for stx, the eae variant (subtype) and the biomarker gene for a given serogroup are evaluated. The PCR results can be "positive", "negative" or "unusable". In this algorithm, the stx genes encoding Shiga toxins are the priority targets, so that a negative PCR result for these genes leads to a negative final result, no matter what the PCR result for the eae and biomarker genes are. The final result can be "positive" (STEC present), "negative" (STEC absent) or "invalid" (in which case the assay should be repeated). A positive final result requires a positive PCR result for all three target genes.

The algorithm is performed by a software stored in the control means of the modified apparatus 10 according to the present invention.

The inventive apparatus 10 further comprises indicator, e.g., display means (not shown) for optically and/or acoustically indicating, e.g., displaying the final result for each STEC serogroup.

EXAMPLES

Sample Preparation

A food sample to be checked for the presence or absence of one or more specific serogroups of Shiga toxin-producing E. coli was incubated in a conventional culture medium (e.g., buffered peptone water) prewarmed at 41.5±1° C. to enable growth of E. coli yielding an enriched sample (E. coli stock medium). 50 µL portions of the enriched sample were transferred into a prefilled lysis plate comprising 96 tubes each of which is prefilled with 500 µL of Chelex-100 diluted to 20% by weight in water. After closure of the tubes with an aluminium sheet, the lysis plate is placed for 10 min in a thermal block preheated to 102±2° C. When the lysis step is completed, the aluminium sheet is pierced with a tip to collect 36 µL portions of lysate which are transferred to a 6-sector disc reaction cartridge.

The remaining E. coli stock medium is stored at 5±3° C. for use in the subsequent verification step.

GeneDisc PCR Assays

The lysates are allowed to sit at room temperature for 5 min, then loaded into the reaction cartridge (i.e., one sample per sector). Each sector of this STEC Top7 GeneDisc comprises 6 individual wells, containing dehydrated primers and probes enabling the detection of 14 target genes (see Tables 1 and 2, wherein the serogroups stand for the respective biomarker genes).

Fluorimetric detection of the PCR products is enabled by the use of probes labelled with one of the two fluorophores (reporters) FAM (=carboxy-fluorescin) and ROX (=carboxyrhodamin), so that each well can be used for amplification of two or three genes.

TABLE 1

Configuration of a STEC Top7 GeneDisc sector.

| Well ID | Reporter FAM | Reporter ROX |
|---|---|---|
| 1 | O145 | inhibition control |
| 2 | eae ε | stx1 & stx2 |
| 3 | eae β | eae γ |
| 4 | eae θ | O111 |
| 5 | O157 | O26 |
| 6 |  | O45/O103/O121 |

TABLE 2

Sequence ID numbers of the primers and probes used in the GeneDisc assay. The nucleotide sequences are disclosed in the attached sequence listing.

| Designation of the primers and probes | Sequence ID number |
|---|---|
| inhibition control forward primer | SEQ ID NO: 1 |
| inhibition control reverse primer | SEQ ID NO: 2 |
| inhibition control probe | SEQ ID NO: 3 |
| O26 forward primer | SEQ ID NO: 4 |
| O26 reverse primer | SEQ ID NO: 5 |
| O26 probe | SEQ ID NO: 6 |
| O45 forward primer | SEQ ID NO: 7 |
| O45 reverse primer | SEQ ID NO: 8 |
| O45 probe | SEQ ID NO: 9 |
| O103 forward primer | SEQ ID NO: 10 |
| O103 reverse primer | SEQ ID NO: 11 |
| O103 probe | SEQ ID NO: 12 |
| O111 forward primer | SEQ ID NO: 13 |
| O111 reverse primer | SEQ ID NO: 14 |

TABLE 2-continued

Sequence ID numbers of the primers and probes used in the GeneDisc assay. The nucleotide sequences are disclosed in the attached sequence listing.

| Designation of the primers and probes | Sequence ID number |
|---|---|
| O111 probe | SEQ ID NO: 15 |
| O121 forward primer | SEQ ID NO: 16 |
| O121 reverse primer | SEQ ID NO: 17 |
| O121 probe | SEQ ID NO: 18 |
| O145 forward primer | SEQ ID NO: 19 |
| O145 reverse primer | SEQ ID NO: 20 |
| O145 probe | SEQ ID NO: 21 |
| O157 forward primer | SEQ ID NO: 22 |
| O157 reverse primer | SEQ ID NO: 23 |
| O157 probe | SEQ ID NO: 24 |
| eae β forward primer | SEQ ID NO: 25 |
| eae β reverse primer | SEQ ID NO: 26 |
| eae β probe | SEQ ID NO: 27 |
| eae γ forward primer | SEQ ID NO: 28 |
| eae γ reverse primer | SEQ ID NO: 29 |
| eae γ probe | SEQ ID NO: 30 |
| eae θ forward primer | SEQ ID NO: 31 |
| eae θ reverse primer | SEQ ID NO: 32 |
| eae θ probe | SEQ ID NO: 33 |
| eae ε forward primer | SEQ ID NO: 34 |
| eae ε reverse primer 1 | SEQ ID NO: 35 |
| eae ε reverse primer 2 | SEQ ID NO: 36 |
| eae ε probe | SEQ ID NO: 37 |
| stx1 forward primer | SEQ ID NO: 38 |
| stx2 forward primer | SEQ ID NO: 39 |
| stx1 reverse primer | SEQ ID NO: 40 |
| stx2 reverse primer 1 | SEQ ID NO: 41 |
| stx2 reverse primer 2 | SEQ ID NO: 42 |
| stx2 probe | SEQ ID NO: 43 |
| stx1 probe | SEQ ID NO: 44 |

For each sample, the PCR results of the different target genes which are obtained by the fluorimetric detection are evaluated according to an algorithm by a software running in the GeneDisc Cycler. Table 3 shows the algorithm results as a function of the PCR results for a given serogroup. In this algorithm, stx1 and stx2 are the priority targets, so that a negative PCR result for these genes leads to a negative final result, no matter what the PCR result for the eae and biomarker genes are.

TABLE 3

Algorithm for evaluation of PCR results.

| PCR result for target genes (1 = positive, 2 = negative, 3 = unusable) | | | Final result for a given serogroup | |
|---|---|---|---|---|
| stx1 and/or stx2 | eae variant | Serogroup biomarker | Algorithm result | Color code |
| 2 | 1 or 2 or 3 | 1 or 2 or 3 | 2 | GREEN |
| 1 or 3 | 2 | 1 or 2 or 3 | 2 | GREEN |
| 1 or 3 | 1 or 2 or 3 | 2 | 2 | GREEN |
| 1 | 1 | 1 | 1 | RED |
| 1 | 1 | 3 | 3 | GREY |
| 1 | 3 | 1 | 3 | GREY |
| 1 | 3 | 3 | 3 | GREY |
| 3 | 1 or 3 | 1 or 3 | 3 | GREY |

The fully automated PCR evaluation allows to indicate, especially to display a final result for each of the STEC Top7 serogroups to be detected, so that the user does not need to evaluate the PCR results for the single genes by himself. The final result is preferably displayed as a color code, i.e., GREEN for the absence of the STEC serogroup, RED for the presence of the STEC serogroup, and GREY for an invalid result (in which case the assay should be repeated).

An additional evaluation of the inhibition control may indicate that a PCR inhibitor is present in the sample solution, in which case the assay should be repeated after a 1:10 dilution.

Immunoconcentration-PCR (IMC-PCR)

In case of a positive PCR result in the GeneDisc assay, 100 µL to 1 mL of enriched sample were incubated with specific antibodies for one of the presumptive positive STEC Top7 to prepare an immunoconcentrate. After 1 to 4 washing steps, the concentrated cells (immunoconcentrate) were eluted with PBS comprising 0.05% by weight of Tween 20. Half of the cells are used for PCR analysis with the STEC Top7 GeneDisc plates. In case of a positive result for the targeted genes, the remaining part of the cells are plated on specific chromogenic agar media. Up to 6 isolated colonies are tested with the STEC Top7 GeneDisc for a final confirmation.

The inventive method (also referred to as "GeneDisc STEC Top7 method" in the following) was tested on raw beef meat (25 g and 375 g) and raw dairy products (25 g).

Example 1

Raw Beef Meat (25 g)

The GeneDisc STEC Top7 method was evaluated on 2,476 fresh minced beef samples collected in supermarkets of 92 departments of France. 25 g of each sample were admixed with 225 mL of buffered peptone water then incubated at 37° C. for 18 h to 24 h. After PCR screening, bacterial isolation by direct plating was performed from PCR positive samples, according to the ISO 13136 technical specification recommendations. The purpose of this study was to compare the screening approach described in the ISO 13136 technical specification (stx, eae and serogroup) to the STEC Top7 screening approach including the eae variants (subtypes) instead of the generic eae gene. The results are reported in Table 4.

TABLE 4

Evaluation of the entire GeneDisc STEC Top7 method with 2,476 naturally contaminated fresh minced beef samples.

| Screening steps | Fresh minced beef Number | Prevalence % |
|---|---|---|
| Total number of samples | 2,476 | 100 |
| stx$^+$, eae$^+$, Top7$^+$ | 84 | 3.4 |
| stx$^+$, eae variant$^+$, Top7$^+$ | 29 | 1.2 |
| Colony isolation | 7 | 0.3 |

This Example demonstrates that the first screening of eae variant genes associated to serogroup encoding genes and stx genes allowed to significantly decrease the number of PCR positive samples from 84 to 29. Indeed, the rates of PCR positive samples for the ISO 13136 approach and the GeneDisc STEC Top7 method were 3.4 and 1.2%, respectively.

Example 2

Raw Dairy Products (25 g)

The GeneDisc STEC Top7 method was evaluated on 1,448 raw dairy products including 1,072 raw milk samples and 376 raw milk cheeses. 25 g of each sample were diluted in 225 mL of buffered peptone water supplemented with novobiocin (10 mg/L). Samples were incubated at 37° C. for 18h+2h. The purpose of this Example was to compare the screening approach described in the ISO13136 technical specification (stx, eae and serogroup) to the STEC Top7 screening approach including the eae variants instead of the generic eae gene. The results are reported in the Table 5.

TABLE 5

Evaluation of the entire GeneDisc STEC Top7 method with 1,448 naturally contaminated raw dairy samples.

| Screening steps | Raw milk Number | Raw milk Prevalence % | Raw milk cheese Number | Raw milk cheese Prevalence % | Global prevalence |
|---|---|---|---|---|---|
| Total number of samples | 1,072 | 100 | 376 | 100 | 100 |
| stx$^+$, eae$^+$, Top7$^+$ | 245 | 22.9 | 160 | 42.6 | 28.0 |
| stx$^+$, eae variant$^+$, Top7$^+$ | 163 | 15.2 | 104 | 27.7 | 18.4 |
| IMC-PCR conform | 40 | 3.7 | 36 | 9.6 | 5.2 |
| Colony isolation | 7 | 0.7 | 6 | 1.6 | 0.9 |

The results showed again that the detection of eae variant genes in first screening allowed to decrease the rate of PCR positive samples by 33.6% and 35.0% in raw milk samples and raw milk cheeses, respectively. The second screening step of the STEC Top7 method, based on IMC-PCR, induced a significant decrease of presumptive positive samples by 75.7% and 65.3% in raw milk samples and in raw milk cheese samples, respectively, indicating that in most samples the different targeted genes should be carried by different *E. coli* strains.

Example 3

Raw Beef Meat (375 g)

Evaluation of the entire method was also realized on 375 g raw beef meat samples, including 400 ground beef samples and 150 beef trim samples processed in 4 facilities across the US. The inventive GeneDisc method was compared to the USDA-FSIS MLG 5B.01 method. 375 g of each sample were diluted in either 1.5 L of mTSB or 975 mL of mTSB with novobiocin (mTSBn). Samples were incubated at 42° C. The incubation time depended on the enrichment broth: 12 h for the mTSB, 15 h for the mTSBn. Presumptive positive samples were confirmed according to reference methods (USDA-FSIS MLG 5 & 5B.01). The results are reported in Table 6.

TABLE 6

Evaluation of the entire GeneDisc STEC Top7 method with 550 naturally contaminated raw beef meat samples.

| Sample type | Enrichment broth | GeneDisc STEC Top7 method | | USDA-FSIS method MLG 5 & 5B.01 | |
|---|---|---|---|---|---|
| | | PCR positive samples | Confirmation | PCR positive samples | Confirmation |
| Ground Beef | mTSB (12 h) | 0/400 | NA | 0/400 | NA |
| | mTSBn (15 h) | 1/400 | 1/1 (O157) | 9/400 | 1/8 (O157) |
| Beef Trim | mTSB (12 h) | 1/150 | 1/1 (O26) | 0/150 | NA |
| | mTSBn (15 h) | 1/150 | 1/1 (O26) | 1/150 | 0/1 |
| Prevalence | | 0.36% | 0.36% | 1.82% | 0.18% |

Among 400 ground beef samples, the GeneDisc STEC Top7 method gave only 1 presumptive positive sample from the mTSBn enrichment. This presumptive result was confirmed by culture method. The USDA-FSIS method detected 9 potential positive samples. Only 1 was confirmed by the culture method. The sample naturally contaminated with STEC O157 was detected by both methods and confirmed by culture.

Among 150 beef trim samples, the GeneDisc method detected 1 potential positive sample enriched either in mTSB or in mTSBn which were confirmed by the culture method. The USDA-FSIS MLG 5B.01 method detected 1 other potential positive sample enriched in mTSBn which was not confirmed. More interestingly, the presumptive positive sample by the GeneDisc method, confirmed by culture, was not detected by the PCR screening of the USDA-FSIS MLG 5B.01 method. The GeneDisc STEC Top7 method and the reference method gave 2 and 10 presumptive positive samples, respectively. Cultural confirmation of all samples yielded 3 Top7 STEC isolates whose 2 were given as presumptive positive samples by the GeneDisc method (O157 and O26). Only 1 of the presumptive positive samples obtained by the reference method was confirmed (O157). The prevalence of the GeneDisc and the USDA-FSIS methods were 0.36% and 1.82%, respectively.

Table 7 demonstrates in a summary the important differences of the inventive method and the method of ISO/TS 13136:2012.

TABLE 7

| Sample Type | Fresh minced beef (25 g) | Raw milk (25 g) | Raw milk cheese (25 g) |
|---|---|---|---|
| Number of samples tested | 2,476 | 1,072 | 376 |
| Reduction of positive samples due to eae variant screening | 65.5% | 33.5% | 35.0% |
| Reduction of positive samples due to IMC-PCR | ND | 75.5% | 65.4% |

The invention claimed is:

1. A method for determining the presence or absence of one or more specific serogroups of pathogenic Shiga toxin-producing E. coli (STEC) in a food sample, comprising
incubating the food sample in a culture medium enabling growth of E. coli to obtain an E. coli stock medium;
performing a lysis of the E. coli in the stock medium to obtain a sample solution comprising E. coli DNA; and
subjecting the sample solution to a first series of polymerase chain reactions (PCR), using primers to amplify the following E. coli genes or fragments thereof:
stx1 and/or stx2 encoding Shiga toxin 1 and Shiga toxin 2, respectively,
for each STEC serogroup to be determined, the subtype of the eae gene of that serogroup, and
for each STEC serogroup to be determined, a biomarker gene specific for that serogroup;
and, in case that stx1 and/or stx2 as well as the eae gene and the specific biomarker gene for at least one serogroup are amplified in the first series of PCRs:
verifying the presence of the one or more specific serogroups of STEC by performing a second series of PCRs on concentrates of the E. coli stock medium and, optionally, a third series of PCRs on single E. coli colonies derived from the concentrates.

2. The method of claim 1, wherein the verification of the presence of the one or more specific serogroups of STEC comprises
performing an immunoconcentration of the E. coli stock medium for each serogroup, using antibodies directed against the STEC of the respective serogroup;
isolating DNA from the immunoconcentrates; and
subjecting the DNA to a second series of PCRs, using primers to amplify the following E. coli* genes or fragments thereof:

stx1 and/or stx2, the subtypes of the eae gene of the respective serogroups, and optionally, the biomarker genes specific for the respective serogroups.

3. The method of claim 2, wherein the verification of the presence of the one or more specific serogroups of STEC further comprises, in case that stx1 and/or stx2 as well as the eae genes are amplified in the second series of PCRs:

plating the immunoconcentrates on a chromogenic medium to enable growth of isolated *E. coli* colonies;

isolating DNA from the isolated colonies; and subjecting the DNA to a third series of PCRs, using primers to amplify the following *E. coli* genes or fragments thereof:

stx1 and/or stx2, the subtypes of the eae gene of the respective serogroups, and optionally, the biomarker genes specific for the respective serogroups.

4. The method of claim 2, wherein at least one series of PCRs is performed with specific labeled DNA probes to allow detection of the amplified genes or fragments.

5. The method of claim 2, wherein the specific serogroups to be determined are selected from O157, O26, O45, O103, O111, O121 and O145.

6. The method of claim 3, wherein the chromogenic medium is selected from Cefixime-Tellurite Sorbitol McConkey (CT-SMAC); Tryptone Bile X Glucuronide medium (TBX); and Cefixime-Tellurite Rhamnose McConkey (CT-RMAC).

7. The method of claim 3, wherein at least one series of PCRs is performed with specific labeled DNA probes to allow detection of the amplified genes or fragments.

8. The method of claim 3, wherein the specific serogroups to be determined are selected from O157, O26, O45, O103, O111, O121 and O145.

9. The method of claim 1, wherein at least one series of PCRs is performed with specific labeled DNA probes to allow detection of the amplified genes or fragments.

10. The method of claim 9, wherein the specific serogroups to be determined are selected from O157, O26, O45, O103, O111, O121 and O145.

11. The method of claim 1, wherein the specific serogroups to be determined are selected from O157, O26, O45, O103, O111, O121 and O145.

12. The method of claim 11, comprising the determination of the presence or absence of serogroups O157, O26, O45, O103, O111, O121 and O145.

13. The method of claim 11, comprising determining at least two subtypes of the eae gene selected from eae $\beta$ for O26; eae $\gamma$ for O145 and O157; eae $\epsilon$ for O45, O103 and O121; and eae $\theta$ for O111.

14. The method of claim 1, wherein the specific biomarker genes are selected from the O-antigen transporter genes of the respective serogroups.

15. The method of claim 1, wherein the food sample is selected from raw meat, raw beef, a raw dairy product, or a raw vegetable product.

16. The method of claim 15, wherein the raw vegetable product is a spout.

17. The method of claim 1, wherein the culture medium for the incubation step is selected from buffered peptone water, optionally comprising acriflavine; tryptic soy broth (TSB), optionally comprising novobiocine; and modified tryptic soy broth (mTSB), optionally comprising novobiocine.

18. The method of claim 1, wherein the PCRs of each series are performed simultaneously in an automated manner.

* * * * *